US00PP37750P3

(12) United States Plant Patent
Olesen

(10) Patent No.: US PP37,750 P3
(45) Date of Patent: Oct. 13, 2026

(54) MINIATURE ROSE PLANT NAMED 'POULTY041'

(50) Latin Name: *Rosa hybrida*
Varietal Denomination: Poulty041

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 48 days.

(21) Appl. No.: 18/831,807

(22) Filed: Sep. 15, 2025

(65) Prior Publication Data

US 2026/0083030 P1 Mar. 19, 2026

(30) Foreign Application Priority Data

Sep. 19, 2024 (QZ) ..... PBR 2024/2194

(51) Int. Cl.
*A01H 5/02* (2018.01)
*A01H 6/74* (2018.01)

(52) U.S. Cl.
USPC ..... Plt./116
CPC ..... *A01H 6/749* (2018.05); *A01H 5/02* (2013.01)

(58) Field of Classification Search
USPC ..... Plt./116, 121, 132, 143
CPC . A01H 5/02; A01H 5/00; A01H 6/749; A01H 6/74
See application file for complete search history.

(56) References Cited

U.S. PATENT DOCUMENTS

PP23,604 P3 * 5/2013 Olesen ..... A01H 6/749 Plt./116

OTHER PUBLICATIONS

Poulsen Roser A/S Vikki retrieved on Nov. 18, 2025 at https://www.poulsenroser.dk/en/Roses/ShowProduct/85407, 2 pp. (Year: 2025).*

* cited by examiner

*Primary Examiner* — June Hwu

(57) ABSTRACT

A new garden rose plant of the Miniature class which has abundant, mauve pink flowers with intonations of red-purple at the petal margin. This new and distinct variety has shown to be uniform and stable in the resulting generations from asexual propagation.

2 Drawing Sheets

Botanical designation: *Rosa hybrida.*
Variety denomination: 'Poulty041'.

This application claims priority to Plant Breeder's Rights Application Number 2024/2194, which was filed at the Community Plant Variety Rights Office in the European Union on Sep. 19, 2024, the contents of which are hereby incorporated by reference for all purposes.

BACKGROUND OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2017 and the resulting seeds were planted in a controlled environment in Odense, Denmark. The new variety, named 'Poulty041', originated as a single seedling from the stated cross.

The new variety may be distinguished from its male pollen parent and female seed parent primarily by the following characteristics. The male pollen parent plant has pink flowers while the new variety has mauve pink flowers with marginal intonations of red-purple. The female seed parent plant has light pink flowers while the new variety has mauve pink flowers.

SUMMARY OF THE INVENTION

The objective of the hybridization of this rose variety was to create a new and distinct variety with unique qualities, such as:

1. Uniform and abundant mauve pink flowers showing marginal intonations of red-purple with long shelf-life;
2. Suitability for commercial production in containers;
3. Early flowering; and
4. Vigorous, but compact growth when propagated on its own roots;

This combination of qualities is not present in previously available commercial cultivars of this type, known to the inventor, and distinguish 'Poulty041' from all other varieties of which we are aware.

As part of the rose development program, Mogens N. Olesen germinated the seeds from the aforementioned hybridization during winter of 2017 and conducted evaluations on the resulting seedlings in a controlled environment in Odense, Denmark. 'Poulty041' was selected in the spring of 2018 by the inventor as a single plant from the progeny of the aforementioned hybridization.

Asexual reproduction of 'Poulty041' by rooted cuttings was first done by Mogens N. Olesen in the nursery in Odense, Denmark in July, 2018. This initial and other subsequent asexual propagations conducted in controlled environments have demonstrated that the characteristics of 'Poulty041' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty041'.

Specifically illustrated in FIG. 1 of the drawings are open flowers viewed from above and the side; and flower petals and sepals detached from the receptacle, showing reproductive flower parts.

Figure 1:
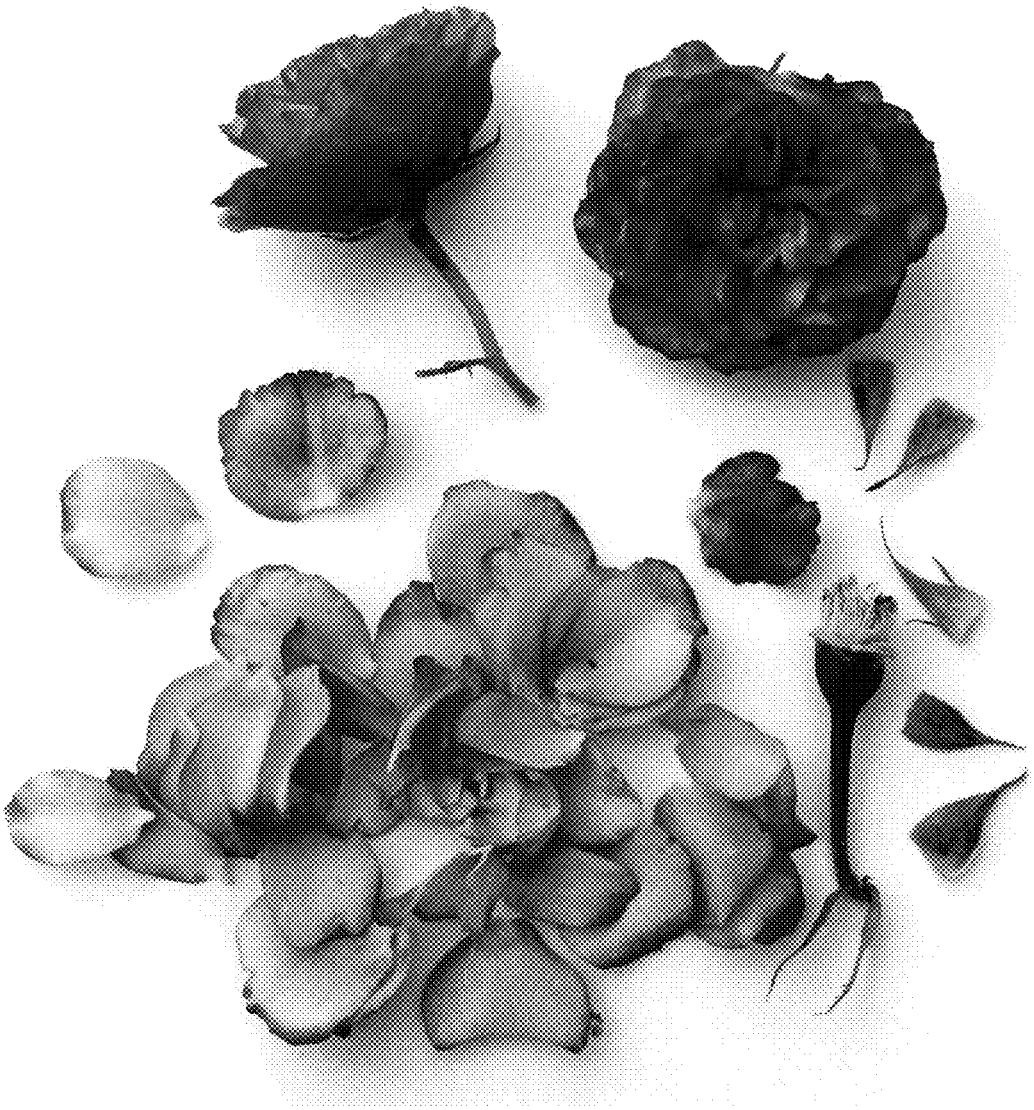
Figure 2:
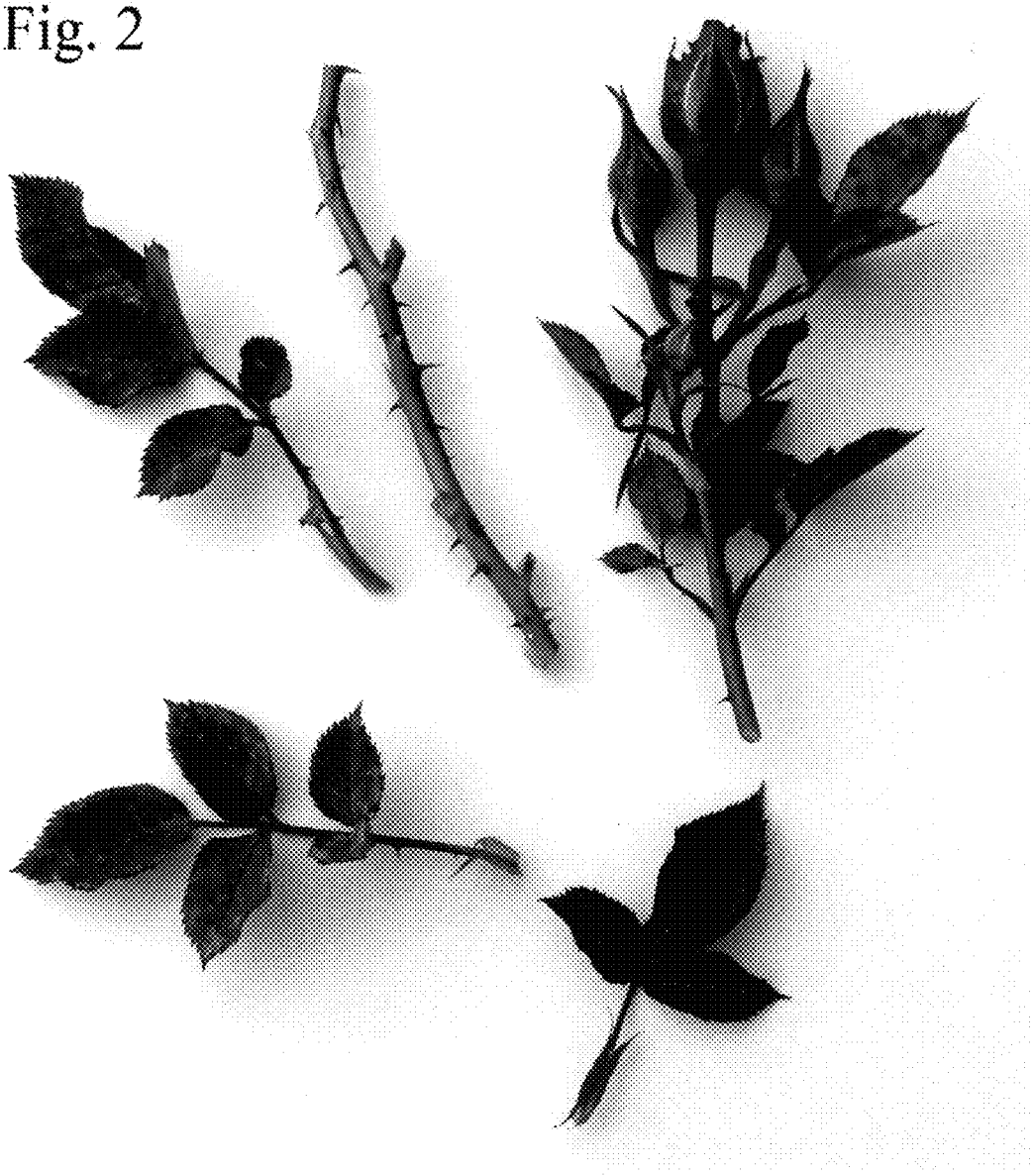

Specifically illustrated in FIG. 2 of the drawings are a cluster of flower buds on a branch, a bare branch exhibiting prickles, and leaves. Plants shown are 12 months of age.

DETAILED DESCRIPTION OF THE VARIETY

The following is a description of 'Poulty041', as observed in its growth in an outdoor hoop house nursery in Half Moon Bay, California. Observed plants are 12 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poulpar058', U.S. Plant Pat. No. 23,604, are compared to the claimed plant. While 'Poulty041' has 40 flower petals, 'Poulpar058' has 18 to 20 flower petals. The claimed plant will normally exhibit 3 to 5 flowers on a single branch, while the comparison variety usually produces a single flower per branch. For the claimed plant, the upper petal surface of outer petals is described as being Red-Purple Group 69B with marginal intonations of Red-Purple Group 61A and Red-Purple Group 61B. The upper petal surface or outer petals of 'Poulpar058' are Purple Group 75A.

Flower and Flower Bud

Blooming habit: Continuous.

Flower bud:

*Size*.—Upon opening, 23 mm in length from base of receptacle to end of bud. Bud diameter is 12 mm.

*Bud form*.—Urceolate.

*Bud color*.—As sepals begin to divide petals are Red-Purple Group N57A.

*Sepal inner surface*.—Color: Yellow-Green Group 146D with intonations of Greyed-Red Group 180A. Surface: Lightly pubescent.

*Sepal outer surface*.—Color: Yellow-Green Group 144A with intonations of Greyed-Purple Group 183A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—About 25 mm long, 9 mm wide.

*Receptacle*.—Texture: Smooth. Size: 9 mm in height, 10 mm wide. Color: Yellow-Green Group 144A with strong intonations of Greyed-Purple Group 183A. Shape: Campanulate.

*Pedicel*.—Surface: Smooth. Length: About 21 mm. Diameter: 2.5 mm. Color: Greyed-Purple Group 185A. Strength: Strong.

*Peduncle*.—Length: 1 to 3 cm. Diameter: About 3 mm. Color: Yellow-Green Group 145A with intonations of Greyed-Purple Group 183A. Texture: Smooth.

Flower bud development: Flower buds are borne in clusters of 3 to 5 flower buds per stem.

Flower bloom:

*Fragrance*.—Light floral scent.

*Duration*.—The blooms have a duration on the plant of approximately 21 days. Petals fall cleanly away from plant after flowers have fully matured.

*Size*.—Flower diameter is about 65 mm when open. Flower depth is 22 mm.

*Flower shape*.—Open cup, double flower, with petals that curve out from the center.

*Shape of flower, side view*.—The upper portion is flat. The lower portion is deeply concave.

Petalage: Under normal conditions, flowers have about 40 petals.

General tonality of flower: Open flowers are Red-Purple Group 59C and Red-Purple Group 69A.

Petal color:

*Upon opening, outer petals*.—Upper surface: Red-Purple Group 69B with marginal intonations of Red-Purple Group 61A and 61B. Occasional streak Yellow-White Group 158D. Lower surface: Red-Purple Group 69A at the basal and middle zone. At marginal zone Red-Purple Group 61B.

*Upon opening, inner petals*.—Upper surface: Red-Purple Group 69B with marginal intonations of Red-Purple Group 61A and 61B. Lower surface: Basal and middle zone are Red-Purple Group 69A. Marginal zone Red-Purple Group 61B.

*Basal petal spots, upon opening*.—Upper surface: Yellow-White Group 158D. Lower surface: Yellow-White Group 158D.

After opening, outer and inner petals,—Upper surface: Red-Purple Group 69B with marginal intonations of Red-Purple Group 61A and 61B. Lower surface: Basal and middle zone are Red-Purple Group 69A. Marginal zone Red-Purple Group 61B. The lower surface of outer petals is mostly Red-Purple 61A to 61B.

*Basal petal spots, after opening*.—Upper surface: Yellow-White Group 158D, small. Lower surface: Yellow-White Group 158D, small.

Petals:

*Petal reflex*.—None.

*Margin*.—Strong undulations and small clefts.

*Shape*.—Elliptic. Apex shape: Rounded. Base shape: Acute.

*Size*.—About 25 mm (l)×24 to 29 mm (w).

*Texture*.—Somewhat rugose.

*Thickness*.—Average.

Petaloids:

*Size*.—9 mm (l) by 4 mm (w).

*Quantity*.—About 5.

*Shape*.—Elliptical with an acute base and rounded apex.

*Color*.—The upper side is Red-Purple Group 69B with marginal intonations of Red-Purple Group 61A. The lower side is Red-Purple Group 69A with marginal intonations of Red-Purple Group 61B.

Reproductive flower parts:

*Pollen*.—None observed.

*Anthers*.—Size: 2 mm in length. Color: Yellow Group 13D. Quantity: 35 on average.

*Filaments*.—Color: Yellow-Orange Group 14A. Length: 4 mm.

*Pistils*.—Length: 4 mm. Quantity: 28 on average.

*Stigmas*.—Color: Green-White Group 157A.

*Styles*.—Color: Green-White Group 157A.

*Location of stigmas*.—Inferior in location relative to the length of the filaments and the height of the anthers.

*Hips*.—None Observed.

Plant

Plant growth: Upright, with well branched bushy appearance. Plants are 25 cm in height, and about 40 cm wide.

Stems:

*Color of juvenile growth*.—Yellow-Green Group 144B.

*Color of mature growth*.—Yellow-Green Group 144A.

*Length*.—Canes are about 8 to 10 cm from the base of the plant to the flowering portion.

*Diameter*.—About 4 mm.

*Internodes*.—On mature canes about 21 mm between nodes.

*Surface texture*.—Young wood: Smooth. Older wood: Smooth.

Long prickles:

*Incidence*.—About 15 prickles per 10 cm of stem.

*Size*.—Average length of prickles on mature stems is 4 mm.

*Shape*.—Upper portion is linear. Lower portion is concave.

*Color*.—Juvenile prickles: Greyed-Purple Group N186D. Mature prickles: Greyed-Purple Group N186D.

Plant foliage:

*Compound leaf*.—About 90 mm (l)×50 (w).

*Quantity*.—About 3 leaves per 10 cm of stem on average.

*Leaf bearing angle to the stem*.—45 degrees.

*Color of juvenile foliage*.—Upper side: Yellow-Green Group 144A with intonations of Greyed-Purple Group 183A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 1 mm long, 1 mm wide. Quantity: 2 per compound leaf. Shape: Linear, slightly broad based with outward extending apices. Margins: Finely serrated. Color: Yellow-Green Group 144A.

*Petiole*.—Length: 20 mm average. Diameter: 2 mm. Upper surface color: Greyed-Purple Group 183C. Lower surface color: Yellow-Green Group 144A.

*Rachis*.—Length: About 32 mm. Upper surface color: Greyed-Purple Group 183C Lower surface color: Yellow-Green Group 144A.

*Leaflet*.—Quantity: Normally 5 leaflets. Margins: Serrated. Size: Terminal leaflets are about 28 mm long, and 19 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Under normal growing conditions, average resistance to powdery mildew *Sphaerotheca pannosa* var. *rosae*, and downy mildew *Peronospora sparsa*. Above average resistance to rust *Phragmidium* spp., black spot *Diplocarpon rosae*, and *Botrytis cinerea*.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulty041' substantially as described and illustrated herein.

* * * * *